United States Patent
Rendu et al.

(10) Patent No.: US 8,673,215 B2
(45) Date of Patent: Mar. 18, 2014

(54) TEST DEVICE FOR PLATELET AGGREGATION DETECTION

(75) Inventors: Francine Rendu, Paris (FR); Daniel Fruman, Le Pecq (FR); Jaime Levenson, Paris (FR)

(73) Assignee: Centre National de la Recherche Scientifique, Paris (FR)

( * ) Notice: Subject to any disclaimer, the term of this patent is extended or adjusted under 35 U.S.C. 154(b) by 338 days.

(21) Appl. No.: 12/738,795

(22) PCT Filed: Oct. 16, 2008

(86) PCT No.: PCT/IB2008/003346
§ 371 (c)(1),
(2), (4) Date: Jul. 8, 2010

(87) PCT Pub. No.: WO2009/053841
PCT Pub. Date: Apr. 30, 2009

(65) Prior Publication Data
US 2010/0330605 A1 Dec. 30, 2010

(30) Foreign Application Priority Data
Oct. 22, 2007 (EP) .................................... 07291282

(51) Int. Cl.
*G01N 27/00* (2006.01)

(52) U.S. Cl.
USPC .................. 422/82.02; 422/82.01; 422/82.05; 422/82.08; 422/82.09; 422/82.11; 422/73; 422/52; 422/407; 422/501; 422/502; 422/503; 422/504; 436/164; 436/177; 436/43; 436/63; 435/29; 435/4; 435/7.1; 506/30; 250/214.1; 250/251; 250/576; 530/408; 714/752

(58) Field of Classification Search
USPC ......... 422/52, 73, 82.01, 82.05, 82.08, 82.09, 422/82.11, 99, 102, 407, 501, 502, 503, 422/504; 436/164, 177, 43, 63; 506/30; 435/29, 4, 6, 7.1; 250/214.1, 251, 576; 530/408; 714/752
See application file for complete search history.

(56) References Cited

U.S. PATENT DOCUMENTS

| | | | |
|---|---|---|---|
| 6,410,337 B1 * | 6/2002 | Brady et al. | 436/69 |
| 2004/0224419 A1 | 11/2004 | Zheng et al. | 436/69 |

FOREIGN PATENT DOCUMENTS

| | | | |
|---|---|---|---|
| JP | 2004045155 A | * | 2/2004 |
| JP | 2004-257768 | | 9/2004 |

(Continued)

OTHER PUBLICATIONS

Alevriadou et al, "Real-Time Analysis of Shear-Dependent Thrombus Formation and Its Blockade by Inhibitors of von Willebrand Factor Binding to Platelets" Blood, vol. 81, No. 5, Mar. 1, 1993, pp. 1263-1276.*

(Continued)

*Primary Examiner* — Dennis M White
(74) *Attorney, Agent, or Firm* — Fulbright & Jaworski LLP (57) ABSTRACT

The invention relates to the test device for platelet aggregation detection comprising: —an element (1) for receiving a blood sample—a capillary tube (3) connected at a first end (31) to said element (1) and at a second end (32) to a pressure lowering device (5) to pump said blood sample through said capillary tube (3)—at least a pair of facing electrodes (8) on the capillary tube—a device for measuring an impedance between said pair of facing electrodes. The invention also relates to a process for using this device, comprising: a) receiving a blood sample and pumping it through the capillar tube (3) b) determining a dynamic change of the value of the impedance between at least one pair of electrodes (8).

25 Claims, 5 Drawing Sheets

(56) References Cited

FOREIGN PATENT DOCUMENTS

| | | | |
|---|---|---|---|
| JP | 2004257768 A | * | 9/2004 |
| WO | WO 99/08107 | | 2/1999 |
| WO | WO 99/14600 | | 3/1999 |
| WO | WO 2005/059532 | | 6/2005 |

OTHER PUBLICATIONS

International Search Report, issued in Application No. PCT/IB2008/003346, Apr. 16, 2009.

* cited by examiner

TEST DEVICE FOR PLATELET AGGREGATION DETECTION

This application is a national phase application under 35 U.S.C. §371 of International Application No. PCT/IB2008/003346 filed 16 Oct. 2008, which claims priority to European Application No. 07291282.7 filed 22 Oct. 2007. The entire text of each of the above-referenced disclosures is specifically incorporated herein by reference without disclaimer.

The present invention relates to a test device for platelet aggregation detection.

Numerous test devices for exist in the market to perform such detection. The tests are generally performed in specialized laboratories and require a long time to obtain the results.

Most known devices require isolation of platelets from the blood which needs the preparation of a sample. Examples are the trombo aggregometers BIOLA (Moscou) or EMA (Servibio) which use a laser to measure optical transmission through isolated platelets.

Another problem of most known devices is that they require a large amount of blood, for examples those using turbidimetry e.g. a device sold by COULTER (CHRONOLOG) or test devices such as BIOLA or ENTEC MEDICAL, or those using impedance such as another device sold by COULTER or the MULTIPLATE device sold by Instrumentation Laboratory. It is often necessity to dilute the blood samples with an appropriate amount of serum.

There is a need for a test device that is capable of performing routine and ambulatory test i.e. using full (or whole) blood, and preferably without being obliged to dilute the blood sample, and that is capable of giving quick results to respond to ambulatory conditions or to an emergency condition of a patient.

A step toward this aim is performed by the PFA 100 of Dade Behring which measures with full blood the occlusion time of a blood flow through an aperture in the center of a which is membrane coated with aggregating molecules such a collagen, and by the more recent device Verify Now sold by ACCUMETRICS. However, these two devices still require a large amount of blood.

DiaMed has introduced a test by colorimetry in its IMPACT device which can be performed on a small sample of blood (130 µl).

The present invention relates to a test device that is capable of performing an ambulatory test on a small sample of blood, and more particularly of full blood, and of giving a result in a relatively small amount of time, so that it is suitable for ambulatory or emergency conditions.

To that effect, the invention relates to a test device for platelet aggregation detection comprising:
- an element for receiving a blood sample
- a capillary tube connected at a first end to said element and adapted to be connected at a second end to a pressure lowering device to pump said blood sample through said capillary tube
- at least a pair of spaced electrodes, namely placed side by side or face to face, on the capillary tube
- and a connecting device to connect the electrodes to a device for measuring an impedance between said pair of spaced electrodes.

The invention also relates to a system comprised of a said test device and of a measurement unit having at least one impedance measuring device, such as a multimeter, coupled to the connecting device. The system may also comprise a pump coupled to the second end of the capillary tube and/or injection means for adding at least one agent to the blood sample.

The invention also relates to a process for using a test device as defined above, characterized in that it comprises:
a) receiving a blood sample and pumping it through the capillary tube,
b) determining a dynamic change of the value of the impedance (capacitance and/or resistance) between at least one pair of spaced electrodes.

The invention will be better understood with the following description in relation with drawings, wherein.

The normalized variation $\Delta C_n$ is obtained by the formula.

$$\Delta C_n = \Delta C / C_{max}$$

$C_{max}$ being the maximum value of the capacitance obtained when blood is circulating between the electrodes.

The test device illustrated in FIGS. 1a to 1d is comprised of a to hypodermic needle 1 connected by a resilient coupler 2 to an end 31 of a capillary tube 3 which extends along a sinuous path on a glass or plastic support 4 that may be of the size of a credit card. The hypodermic needle and the resilient coupler can be replaced by a blood well where one or more drops of blood may be deposited. The capillary extends along a sinuous or concentric path or any other geometry and has a length allowing shearing the blood sample at a chosen shear rate and time. At the other end 32 of the capillary tube 3 a vane 34 is disposed, to allow a connection of the end 32 to a closed reservoir 5 at a pressure lower than atmospheric pressure to create a pressure difference $\Delta P$ between both ends 31 and 32 of the capillary tube 3 which forms a micro channel along which a collected blood sample is sucked.

Figure 1A:
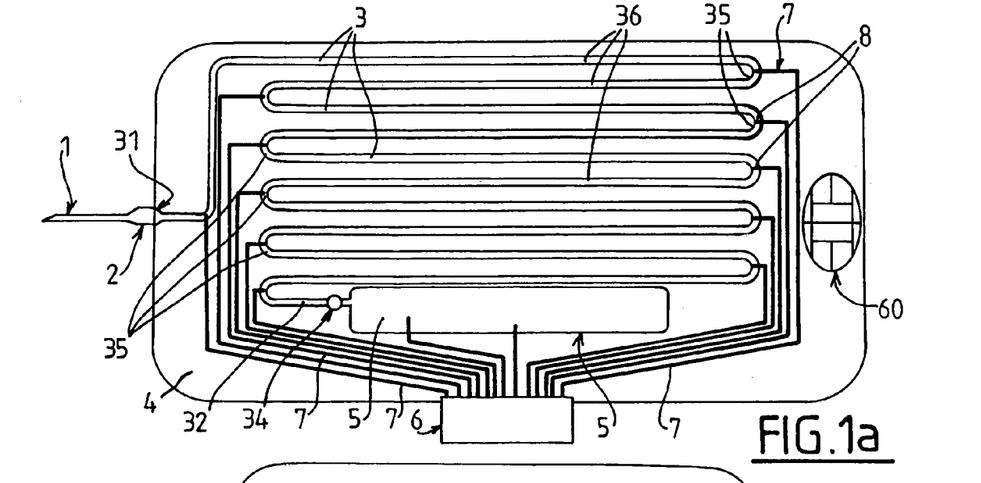
FIG. 1a told illustrate a first embodiment of a test device according to the invention in top view, respectively of the whole device (1a), and of its top (1b), middle (1c), and bottom (1d) layers.

The blood sample thus circulates between ends 31 and 32 where it occupies a part of the length L of the tube 3 and is collected by the reservoir 5. A support 4 with an integrated reservoir 5 allows a self-contained operation for an in situ or ambulatory test.

For the best efficiency, it is recommended that reservoir 5 should be at the lowest pressure that would be compatible with the avoidance of degassing of the blood sample, e.g. 30 mmHg, i.e. about 4000 Pa.

In a variant, a depression or vacuum pump is connected to end 32 of the capillary tube 3, but in this case an integrated reservoir 5 is still desirable to collect the blood, because it allows discarding directly the test device with the blood sample once used.

A connector 6 is electrically coupled to pairs of metal strips 7 on the support 4 to connect to a measuring equipment pairs of electrodes 8 that are spread along the capillary tube 3, for example as shown in curved regions 35 separating linear portions 36 of the capillary tube 3.

The connector 6 allows connecting the pairs of electrodes to the equipment to measure the impedance with a set of conventional multimeters, and more particularly the value of the capacitance C between the pairs of electrodes, as will be discussed in the example below.

It is noted that only a pair of spaced electrodes 8 may be enough. However, using two or more pairs of electrodes 8 along the path of the capillary tube 3 allows obtaining several curves representing the response after subjecting the blood sample to increasing durations of shear, which brings additional information and contributes to the reliability of the test. Two pairs of electrodes may be used to determine the velocity, by determining the time span separating their transient response, and hence the shear rate in the blood sample. With more than two pairs of electrodes, the equipment may comprise only two multimeters: when the measurement starts, the first and second multimeter are coupled to the first and second pairs of electrodes. Then, when the curve representing the passage of blood before the first pair of electrodes has been recorded, the first multimeter is coupled to the third pair of electrodes, and when the curve representing the passage of blood before the second pair of electrodes has been recorded, the second multimeter is coupled to the fourth pair of electrodes and so on.

Figure 1B:
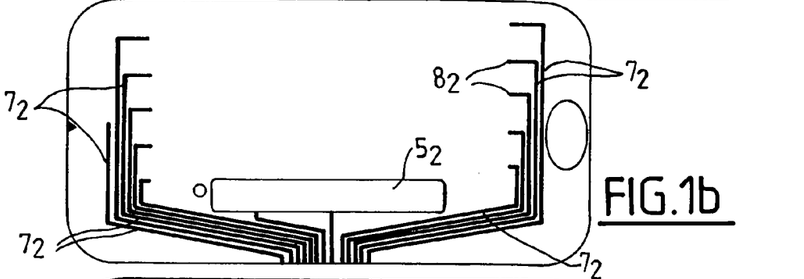
Figure 1C:
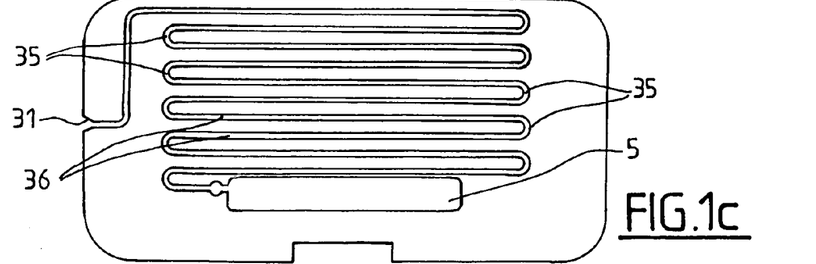
Figure 1D:
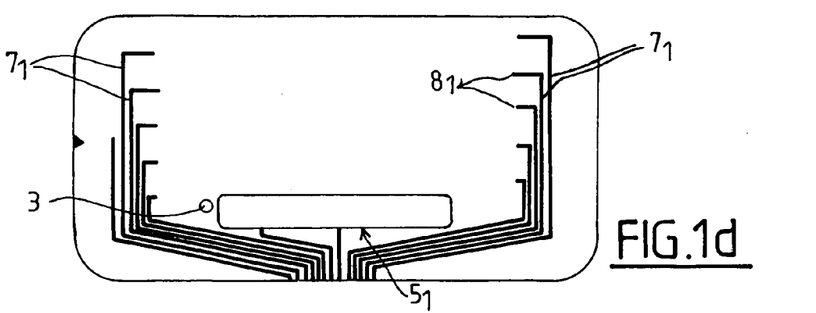

As shown in FIG. 1b-1d, the device is comprised of a sandwich of three layers. The bottom layer (FIG. 1d) is e.g.; made of plastic and comprises a first set of strips made of metal or of or conductive ink $7_1$ having end electrodes $8_1$, an embossed region $5_1$ forming the bottom of the reservoir 5, and an optional spot 34 to lodge an obturator for the channel 3. The middle layer (FIG. 1c) is e.g. made of plastic and comprises an engraved channel 3 (e.g. by high speed water jet) and an engraved reservoir 5. The top layer is similar to the bottom layer (strips $7_2$, electrodes $8_2$ and top region $5_2$). It also comprises an optional opening for an electronic chip 60.

Figure 2:
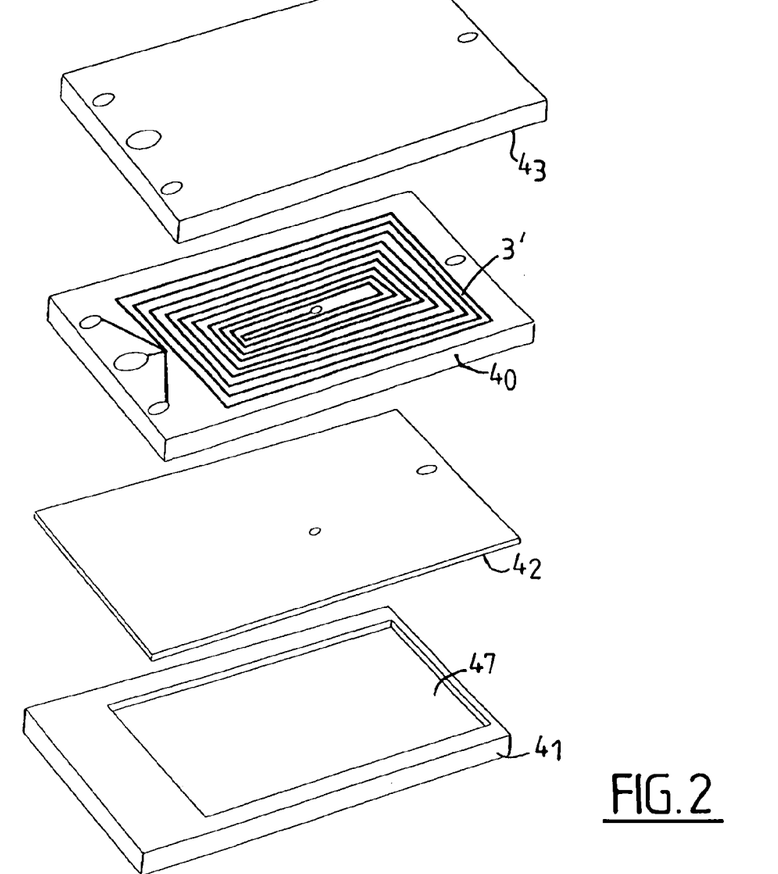
FIG. 2 illustrate another multi-layered embodiment of the invention.
Figure 3:
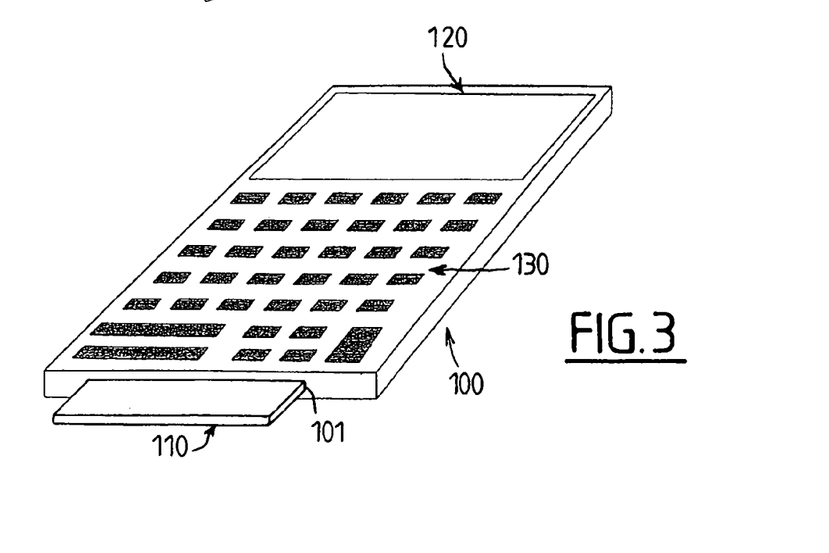
FIG. 3 illustrates a device 110 of the invention connected to a measurement unit 100 having a keyboard 130 and a screen 120.

As shown in the variant of FIG. 2, the support 4 may be comprised of several elements namely a bottom layer $4_1$ having an aperture 47 forming a reservoir, a first isolating plate $4_2$ bearing connecting strips 7, then the main plate $4_0$ comprising the capillary tube 3 with its pairs of measurement electrodes 8 and last a top layer $4_3$ which protects the plates $4_2$ and $4_0$ and may comprise a second set of connecting strips.

In the preferred embodiment of FIGS. 4a-4d, the capillary tube 3' is wound in a helical way, and has a circular, square or rectangular cross section for the circulation of blood. End 32' of the capillary tube 3' in communication with reservoir 5 (FIG. 4c) is located at the center whereas end 31' communicating with the blood well 50 is at the periphery. The volume of this blood well 50 is approximately 30 mm³ to receive a blood sample. Injection tubes 51 and/or 52 may be provided to inject an aggregation agent.

Figures 4A, 4B, 4C, 4D, 5A, 5B:
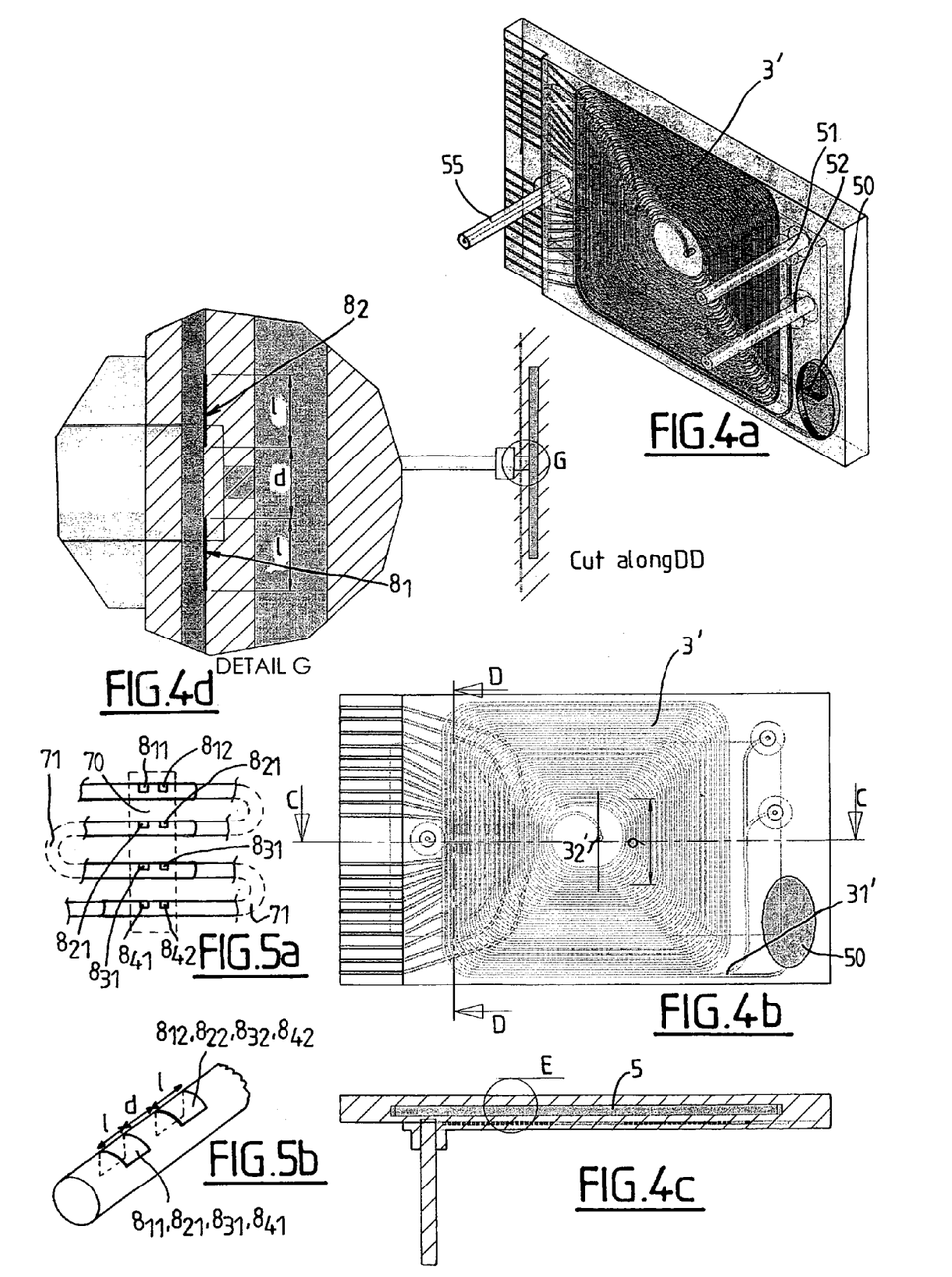
FIGS. 4a to 4d illustrate a preferred embodiment for the test device according to the invention, thereof
FIGS. 5a and 5b illustrate an experimental device and the position of the electrodes of a pair

The inside diameter of the capillary tube 3' is 300μ and its length is 117 cm, to provide a shear rate of about $600^{s-1}$ to a sample of full blood with a difference of pressure ΔP=730 mm Hg (96000 Pa).

FIG. 4a shows the plate $4_0$ in perspective, whereas figure to 4b is a top view of FIG. 4a and FIG. 4c is a cut of FIG. 2c along CC.

FIG. 4d shows a partial cut along DD and detail G thereof to show a pair of electrodes $8_1$ and $8_2$.

Detail G shows two electrodes $8_1$ and $8_2$ of a pair of electrodes placed side by side and separated by a gap d. For example each electrode occupies part of the perimeter of the tube 3' and has a length l=1 mm and width w=0.3 mm, and the electrodes $8_1$ and $8_2$ are separated by a distance d=1 mm.

The tests illustrated in FIGS. 6 to 13b have been performed with an experimental device provided with four pairs of spaced electrodes ($8_{11}$, $8_{12}$; $8_{21}$, $8_{22}$; $8_{31}$, $8_{32}$; and $8_{41}$, $8_{42}$) that are part of a common support 70 shown in FIG. 5a, each electrode $8_{11}$ ... $8_{42}$ having a length l=1 mm and a width w=0.3 mm (see FIG. 5b) and occupying half of the circumference of a capillary tube having an internal diameter of D=300μ. The pairs of electrodes are longitudinally spaced by a distance d=1 mm. A supple capillary tube 71 having a chosen length L is disposed to follow a sinuous path and is in contact with the successive pairs of electrodes.

Figure 6:
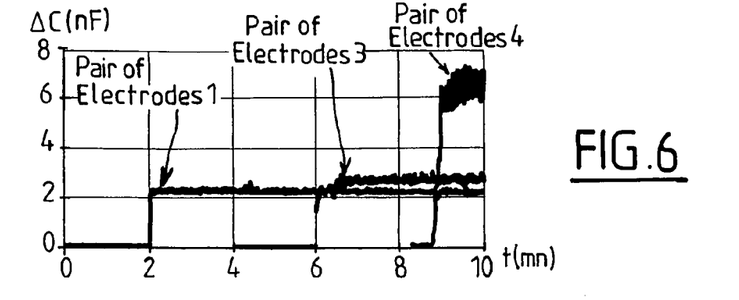
FIGS. 6 to 10, 11a, 11b, 12a to 12c, 13a and 13b illustrate test results obtained with a test device according to FIGS. 4a and 4b. Variation $\Delta C$ (in nF) of capacitance C or normalized variation $\Delta C_n$ of the capacitance is plotted versus time t in minutes or non dimensional time t/T.

FIG. 6 illustrates the change AC in the value of the capacitance with two neutral liquids, namely distilled water and a coloured solution, for three pairs of electrodes.

The passage of the front separating the two liquids produces a sudden variation of the value of the capacitance C. Signals at three pairs of electrodes 1,3 and 4 have been shown.

Figure 7:
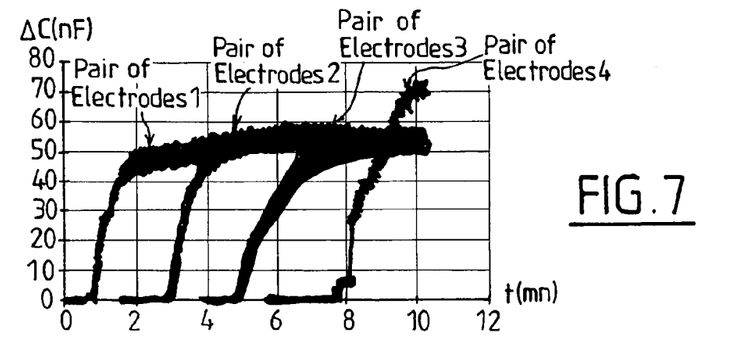

FIG. 7 illustrates the change AC with a flow of distilled water followed by 50% diluted blood with an aggregating agent (collagen at 3 μg/ml), with four pairs of electrodes.

Figure 8:
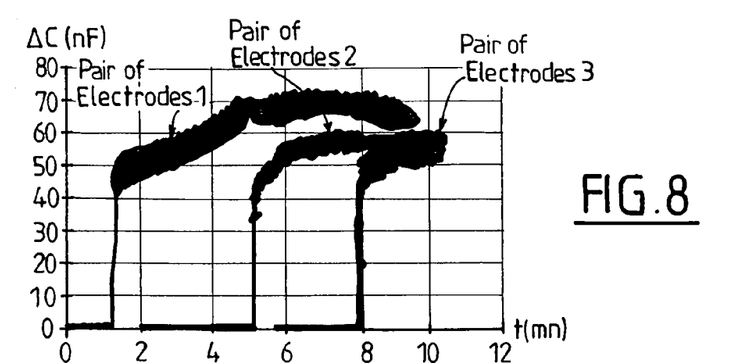

FIG. 8 illustrates a flow of diluted blood that has been incubated during 15 nm with a solution of aspirin at a concentration (5 mM) that is known to inhibit platelet aggregation to which collagen (3 μg/ml) has been added after incubation with signals from three pairs of electrodes 1,2 and 3.

For this sample, aspirin is efficient to prevent aggregation since the change of ΔC exhibits a sudden variation.

Figure 9:
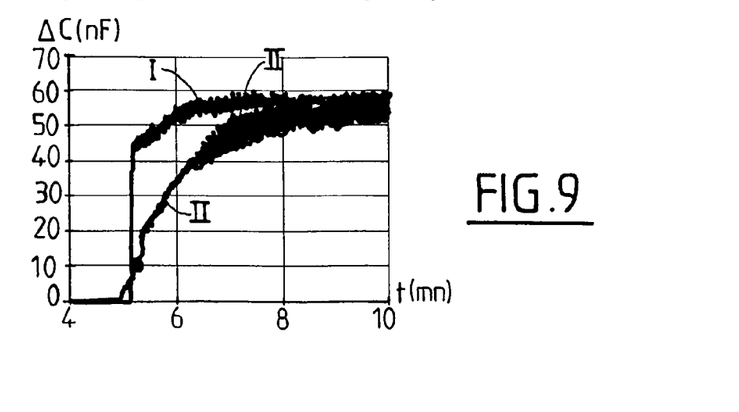

FIG. 9 illustrates a flow of blood that has been incubated (curve I) during 15 mm with aspirin (5 mM) or not incubated (curve II). It can be seen that curve II (no aspirin added) doesn't show the sudden change of curve I, indicating that platelet aggregation may have occurred in curve II, not in curve I.

Figure 10:
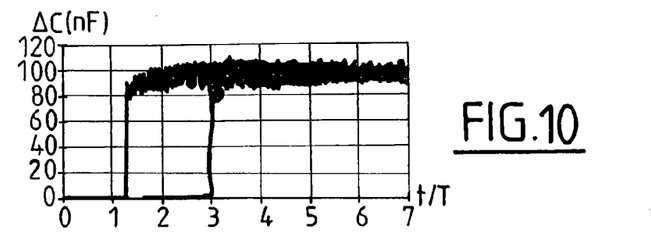

FIG. 10 addresses the specificity of the test with a sample of blood without platelets.

The passage of the sample produces a fast rise ΔC of the value of the capacitance C, which confirms that when a slow transition is present, it is specific of platelets.

Figure 11A:
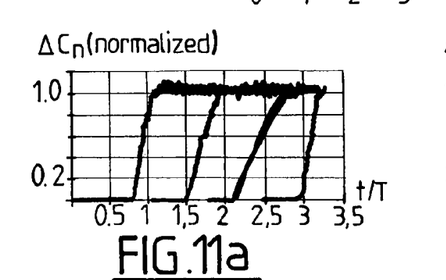
Figure 11B:
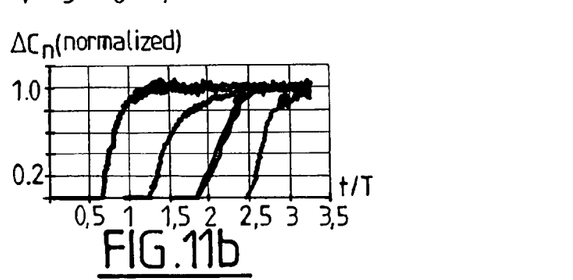

FIGS. 11a and 11b test the influence of an aggregating agent (collagen) on a sample of diluted blood.

FIG. 11a shows curves obtained with a sample without addition of collagen and FIG. 11b shows curves with a sample of the same blood with an addition of collagen (3 μg/ml).

This comparison shows that the main effect is obtained by the shear rate on the sample (around 600 s$^{-1}$ in the example) and that the addition of an aggregating agent may not be necessary. The test device according to the invention may thus be used with a sample of full (or diluted) blood with or without addition of an aggregating agent such as collagen.

Figure 12A:
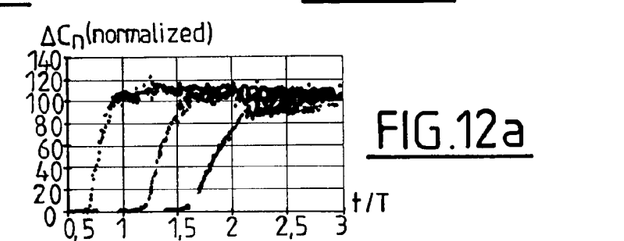
Figure 12B:
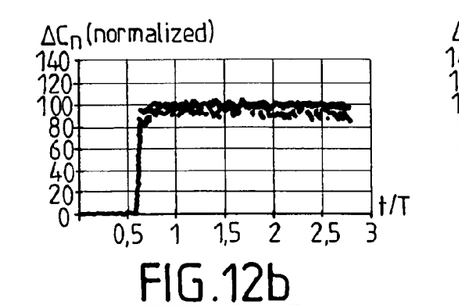
Figure 12C:
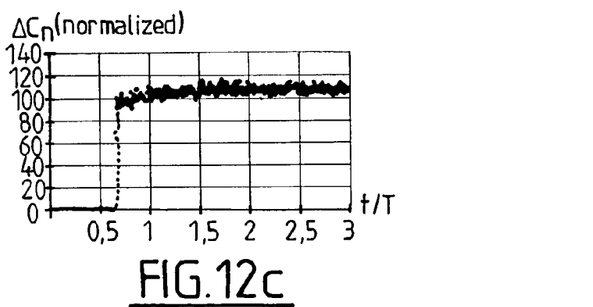

FIGS. 12a to 12c show the effect of a treatment with aspirin. FIG. 9a shows the curve before the treatment. FIGS. 9b and 9c show curves after 3 days of treatment (500 mg/day) respectively without addition of collagen to the sample, and with addition of collagen (3 μg/ml). The sharp change of ΔC in FIGS. 9b and 9c indicates an efficiency of the treatment, independently of the presence of collagen.

Figure 13A:
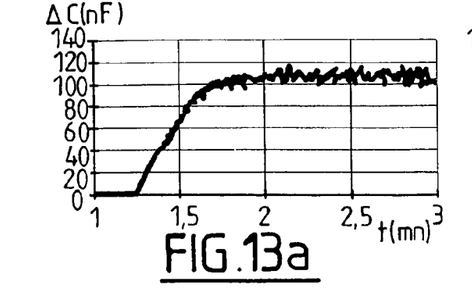
Figure 13B:
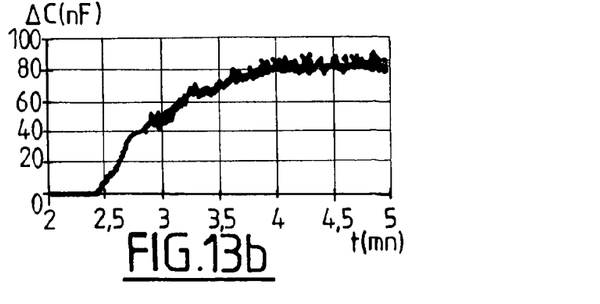

FIG. 13a and FIG. 13b show the correspondence between a test with 50% diluted blood (FIG. 13a) and a test with full blood (FIG. 13b). These curves show that the results are consistent and that the test device may be used either with full blood or with diluted blood.

Tests on full blood are of course preferable for ambulatory or emergency tests. But tests on diluted are also of interest for various reasons, especially since the dilution allows obtaining lower shear rates with the same device.

Another way of obtaining different values of shear rates is providing the capillary tube with two or more lengths of different cross-section. Pressure measurement at the beginning and at the end of each section allows to determine the value of the shear rate in each cross-section.

In the test device, the ratio L/D between the length L and an internal diameter D of a circular capillary tube and S being the internal cross-section of a capillary tube:

$$L/D = \frac{L}{2}\sqrt{\pi/S} \leq \frac{\Delta P}{4\gamma_w \mu}$$

$\gamma_W$ being the minimal shear rate in s$^{-1}$, nominally 200 s$^{-1}$ $\Delta P$ being the maximal pressure differential between both ends of the capillar tube (in Pa), nominally $10^5$ Pa $\mu$ viscosity of the sample (nominally 0.003 Pa·s for a blood sample).

The shear rate of the blood sample in the capillary tube is for example between 200 s$^{-1}$ and 1000 s$^{-1}$, more particularly between 500 s$^{-1}$ and 700 s$^{-1}$, the preferred value being 600 s$^{-1}$. Note that the phenomenon of platelet aggregation depends on the shear rate and the above ranges are pertinent. D is for example between 100 µm and 800 µm and preferably between 100 µm and 500 µm.

The volume of the blood sample is for example between 15 µl and 1 ml (e.g. 100 µl) and it is for example chosen so that the sample occupies only part of the length of the capillary tube.

The maximal transit time in the capillary tube is about 3 minutes. The above formula and the following table allow to adapt the shear rate, the pressure differential $\Delta P$ and the transit time in a capillary tube of length L. The following table shows for different values of the internal diameter D (mm) of the capillary tube and a shear rate of 600 s$^{-1}$ the speed S (mm/s), the flow F (µl/s) and the maximal length $L_{max}$ (m) of the capillary tube for $\Delta P=10^5$ Pa, and the corresponding volume V (µl) of the capillary tube, as well as the Reynolds number R for a viscosity of 3 mPa·s and a volumetric mass of $10^3$ kg/m$^3$

| D (mm) | 0.2 | 0.4 | 0.6 | 0.8 | 1 |
|---|---|---|---|---|---|
| S (mm/s) | 15 | 30 | 45 | 60 | 75 |
| F (µl/s) | 0.47 | 3.77 | 12.72 | 30.16 | 58.9 |
| $L_{max}$ (m) | 2.8 | 5.6 | 8.4 | 11.2 | 14 |
| V (µl) | 88 | 704 | 2380 | 5600 | 11000 |
| R | 1 | 4 | 9 | 16 | 25 |

The test device according to the invention is compatible with a certain degree of miniaturization. Samples of volume lower than 100 µl (e.g. . . . 15 µl which corresponds to a single drop of blood) can be accommodated. Also, sub-millimeter electrodes may be used. L, which is equal to 1 mm in the examples, may be reduced, e.g. to 120 µm, down to about 25 µm.

The invention claimed is:

1. A test device for platelet aggregation detection comprising:
   a blood sample receiving element;
   a capillary tube connected at a first end to said element and adapted to be connected at a second end to a pressure lowering device to pump said blood sample through said capillary tube during use, wherein the pressure lowering device is configured to generate a shear rate $\gamma_w$ of the blood sample in the capillary tube between 200 s$^{-1}$ and 1000 s$^{-1}$ during use;
   at least a pair of facing electrodes on the capillary tube; and
   connecting elements to connect the electrodes to a device for determining a dynamic change of an impedance between said pair of facing electrodes during use, wherein the capillary tube of the test device has a ratio between a length (L) and an internal diameter (D) of:

$$\frac{L}{2}\sqrt{\pi/S},$$

wherein:
S is an internal cross section of the capillary tube; and
the ratio is less than or equal to:

$$\frac{\Delta P}{4\gamma_w \mu},$$

wherein:
$\gamma_w$ is a minimal shear rate in s$^{-1}$ to be achieved during use;
$\Delta P$ is a maximal pressure differential between both ends of the capillary tube (in Pa) during use; and
$\mu$ is a viscosity of the sample during use.

2. The test device of claim 1, wherein the blood sample receiving element is a needle.

3. The test device of claim 1, wherein a plurality of pairs of electrodes are spread on at least part of the length of the capillary tube.

4. The test device of claim 1, wherein the shear rate $\gamma_w$ is between 500 s$^{-1}$ and 700 s$^{-1}$.

5. The test device of claim 4, wherein the shear rate $\gamma_w$ is 600 s$^{-1}$.

6. The test device of claim 1, wherein D is between 100µ and 800µ.

7. The test device of claim 1, wherein D is between 100µ and 500µ.

8. The test device of claim 1, wherein the capillary tube has at least two lengths of different internal cross sections.

9. The test device of claim 1, wherein the blood sample receiving element is a blood well.

10. The test device of claim 1, further comprising a reservoir in communication with the second end of the capillary tube.

11. The test device of claim 10, wherein the reservoir in communication with the second end of the capillary tube is mounted on a support.

12. The test device of claim 1, wherein at least the blood sample receiving element, the capillary tube and a connector in electrical connection with said at least one pair of electrodes are mounted on a multi-layer support.

13. A system comprising a test device of claim 1 and of a measurement unit having at least one impedance measuring device coupled to the connecting device.

14. The system of claim 13, wherein the impedance measuring device is a multimeter.

15. The system of claim 13, further comprising a pump coupled to the second end of the capillary tube.

16. The system of claim 13, further comprising an injector adapted to add at least one agent to the blood sample during use.

17. A process comprising:
   obtaining a test device of claim 1;
   obtaining a blood sample and pumping it through the capillary tube, wherein the shear rate of the blood sample in the capillary tube is between 200 s$^{-1}$ and 1000 s$^{-1}$; and
   determining a dynamic change of the value of the impedance between at least one pair of electrodes.

18. The process of claim 17, wherein the blood sample has a volume between 100 µl and 1 ml.

19. The process of claim 17, wherein the shear rate is between 500 s$^{-1}$ and 700 s$^{-1}$.

20. The process of claim 19, wherein the shear rate is 600 s$^{-1}$.

21. The process of claim 17, wherein the impedance is converted to a capacitance C.

22. The process of claim 17, further comprising adding a treatment agent to the sample in incubating the sample.

23. The process of claim 22, wherein the treatment agent is aspirin.

24. The process of claim 17, further comprising adding an aggregation agent to the sample.

25. The process of claim 24, wherein the aggregation agent is collagen.

* * * * *

UNITED STATES PATENT AND TRADEMARK OFFICE
CERTIFICATE OF CORRECTION

| | | |
|---|---|---|
| PATENT NO. | : 8,673,215 B2 | Page 1 of 1 |
| APPLICATION NO. | : 12/738795 | |
| DATED | : March 18, 2014 | |
| INVENTOR(S) | : Rendu et al. | |

It is certified that error appears in the above-identified patent and that said Letters Patent is hereby corrected as shown below:

In the Claims

Claim 7 column 6, line 35, delete "1" and insert --6-- therefor.

Signed and Sealed this
Sixteenth Day of September, 2014

Michelle K. Lee
*Deputy Director of the United States Patent and Trademark Office*